(12) United States Patent
Wang

(10) Patent No.: US 7,846,147 B2
(45) Date of Patent: Dec. 7, 2010

(54) VULNERABLE PLAQUE TREATMENT

(75) Inventor: Edwin Y. Wang, Tustin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 226 days.

(21) Appl. No.: 10/992,873

(22) Filed: Nov. 18, 2004

(65) Prior Publication Data
US 2006/0106366 A1 May 18, 2006

(51) Int. Cl.
*A61M 31/00* (2006.01)

(52) U.S. Cl. ..................... 604/508; 604/507

(58) Field of Classification Search ........... 604/103.01, 604/507, 508
See application file for complete search history.

(56) References Cited

U.S. PATENT DOCUMENTS

| | | | |
|---|---|---|---|
| 4,113,912 A | | 9/1978 | Okita |
| 5,171,261 A | * | 12/1992 | Noishiki et al. ............ 623/1.41 |
| 5,213,576 A | | 5/1993 | Abiuso et al. |
| 5,547,472 A | | 8/1996 | Onishi et al. |
| 5,935,075 A | * | 8/1999 | Casscells et al. ............ 600/474 |
| 6,171,787 B1 | * | 1/2001 | Wiley .............................. 435/6 |
| 6,395,325 B1 | | 5/2002 | Hedge et al. |
| 6,419,659 B1 | * | 7/2002 | Phelps et al. ............ 604/164.01 |
| 6,491,617 B1 | * | 12/2002 | Ogle et al. ..................... 600/3 |
| 6,624,138 B1 | | 9/2003 | Sung et al. |
| 6,629,947 B1 | | 10/2003 | Sahatjian et al. |
| 7,008,411 B1 | * | 3/2006 | Mandrusov et al. ......... 604/506 |
| 2003/0060877 A1 | * | 3/2003 | Falotico et al. ............. 623/1.42 |
| 2003/0065303 A1 | | 4/2003 | Wellman et al. |
| 2003/0207271 A1 | * | 11/2003 | Holwitt et al. .................. 435/6 |
| 2004/0220607 A1 | * | 11/2004 | Donovan et al. ............ 606/194 |
| 2004/0230156 A1 | | 11/2004 | Schreck et al. |
| 2005/0019404 A1 | | 1/2005 | Sung et al. |
| 2005/0123583 A1 | | 6/2005 | Sung et al. |

OTHER PUBLICATIONS

PCT International Search Report (dated Jun. 2, 2006), International Application No. PCT/US2005/039026—International Filing Date Oct. 28, 2005 (16 pages).

* cited by examiner

*Primary Examiner*—Nicholas D Lucchesi
*Assistant Examiner*—Laura A Bouchelle
(74) *Attorney, Agent, or Firm*—Blakely Sokoloff Taylor & Zafman LLP

(57) ABSTRACT

A method including introducing a treatment device via a transluminal route within a blood vessel to a treatment site including a vulnerable plaque; and dispensing a treatment agent including a compound having a property that tends to modify a property of a content of the vulnerable plaque. A kit including a first treatment agent including a property capable of modifying a property of a content of a vulnerable plaque; and a different second treatment agent. A composition including a treatment agent capable of modifying the mobility of a content of a vulnerable plaque in a form and concentration suitable for dispensing through a catheter into a blood vessel.

52 Claims, 5 Drawing Sheets

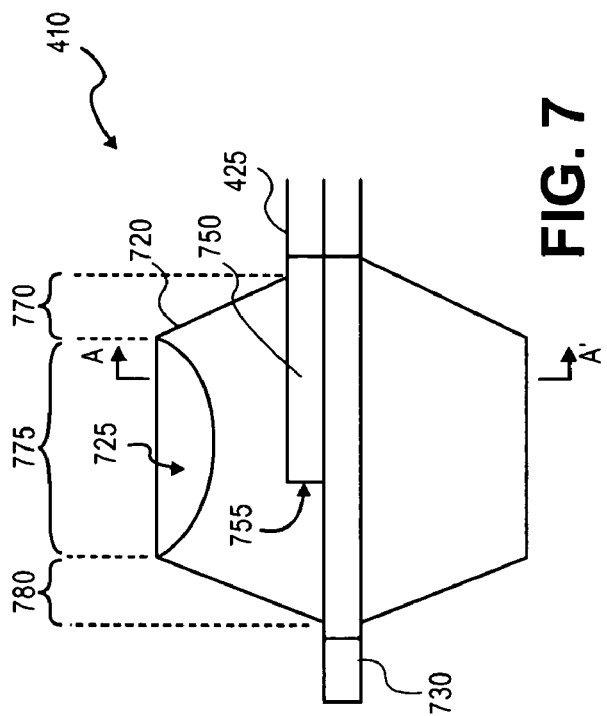
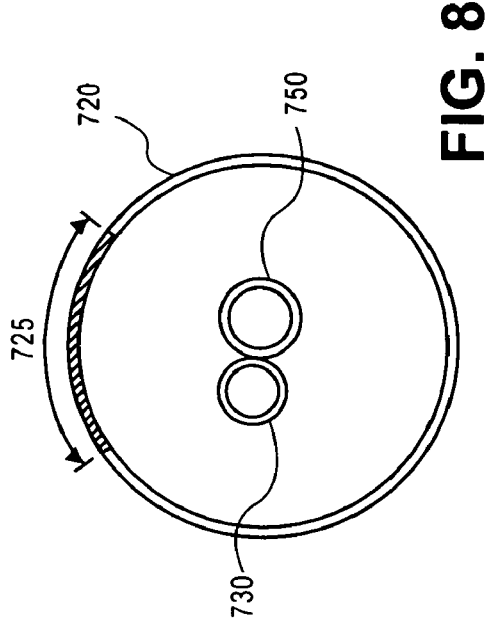
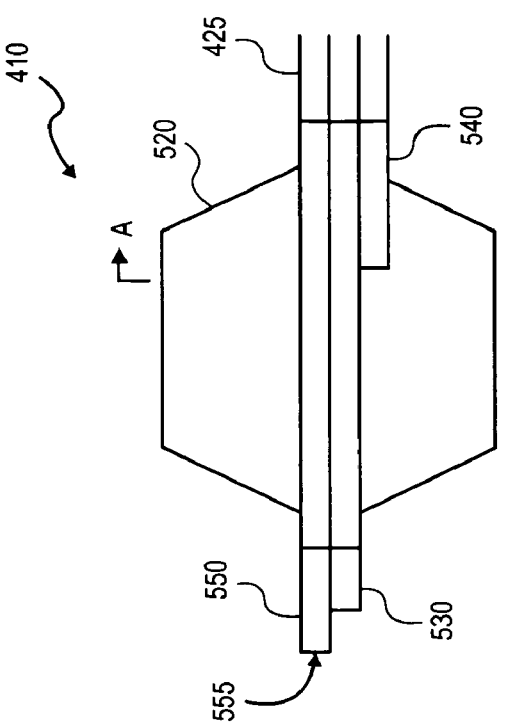
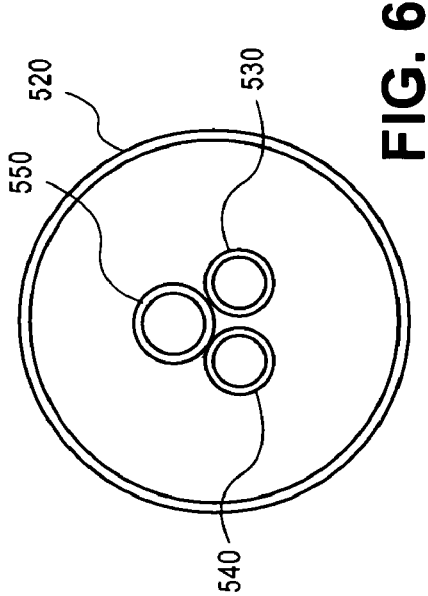

VULNERABLE PLAQUE TREATMENT

FIELD

Transluminal treatment devices, compositions, and methods.

BACKGROUND

Thin-capped fibroatheroma ("TFCA") or vulnerable plaque refers to an atherosclerotic plaque that may develop inside a blood vessel, such as an artery. The typical vulnerable plaque contains a core filled with lipids, cholesterol crystals and cholesterol esters, macrophages, and other cells. The core has a thin fibrous cap (0.05 millimeters (mm) to 0.10 mm thickness). The fibrous cap may become weakened and rupture. When ruptured, the luminal blood becomes exposed to highly thrombogenic material from the core of the vulnerable plaque, which can result in total thrombotic occlusion of the blood vessel.

There is increasing evidence that the propensity of a vulnerable plaque to rupture is related to an activity of matrix metalloproteinases ("MMPs"), largely synthesized by macrophage-derived foam cells. Specifically, MMPs may degrade extracellular matrix proteins, such as Types I and III collagen that are a significant source of fibrous cap structural integrity. Thus, chronic and/or local inflammation, typically a result of monoctye adhesion, in the plaque can lead to destabilization of the vulnerable plaque and acute coronary syndromes (via thrombosis).

Researchers believe that vulnerable plaque is formed in the following way. Fat droplets are absorbed by the blood vessel (e.g., artery), which causes the release of cytokines (proteins) that lead to inflammation. The cytokines make the artery wall sticky, which attracts monocytes (immune system cells). The monocytes squeeze into the artery wall. Once inside, the monocytes turn into macrophages (cells) and begin to soak-up fat droplets. The fat-filled macrophages form a plaque with a thin covering.

Improvements in imaging techniques, such as optical coherence tomography ("OCT") and intravascular ultrasound ("IVUS") offer the opportunity to identify a vulnerable plaque. A need exists, however, for effective methods to treat (e.g., remove, immobilize, reshape) a vulnerable plaque.

SUMMARY

A method is disclosed. In one embodiment, the method includes introducing a treatment device via a transluminal route within a blood vessel to a treatment site comprising a vulnerable plaque; and dispensing a treatment agent comprising a compound comprising a property that tends to modify a property of a content of the vulnerable plaque. Representative properties of the content of the vulnerable plaque include mobility. Suitable compounds include compounds that may act as a cross-linkers that can migrate (e.g., diffuse) into the core of the fibrous cap and cross-link the core materials (e.g., lipids) modifying the core materials from highly thrombogenic to generally non-thrombogenic.

In another aspect, a kit is disclosed. In one embodiment, a kit includes a first treatment agent comprising a property capable of modifying the property of a content of a vulnerable plaque; and a second treatment agent such as an agent that accelerates a cross-linking of a content of a vulnerable plaque and the first treatment agent. In another embodiment, a kit includes a catheter suitable for traversing a blood vessel and having a length dimension suitable for placement at a treatment site within the blood vessel from an externally accessible point of a patient. The first treatment agent and/or the second treatment agent may be introduced through the catheter at a treatment site, including a vulnerable plaque to modify the vulnerable plaque.

In another aspect, a composition is disclosed. The composition includes a treatment agent capable of modifying the mobility of a content of a vulnerable plaque in a form and concentration suitable for dispensing through a catheter into a blood vessel. Examples of a treatment agent capable of modifying the mobility of a content of a vulnerable plaque include cross-linking agents.

In a further aspect, a system is described. In one embodiment, a system includes a system including a reservoir containing a first flowable substance including a cross-linking agent having a property that modifies a core of a vulnerable plaque, and a cannula including a lumen in fluid communication with the first flowable substance in the first reservoir and a distal end portion defining an opening allowing passage out of the distal end portion of the cannula.

BRIEF DESCRIPTION OF THE DRAWINGS

FIG. 5 shows a cross-sectional schematic side view of one embodiment of a distal portion of the catheter assembly of FIG. 4.

FIG. 6 shows a cross-sectional view of the distal portion of the catheter assembly of FIG. 4 through line A-A' of FIG. 5.

FIG. 7 shows a cross-sectional schematic side view of another embodiment of a distal portion of the catheter assembly of FIG. 4.

FIG. 8 shows a cross-sectional view of the distal portion of the catheter assembly of FIG. 4 through line A-A' of FIG. 7.

DETAILED DESCRIPTION

Figure 1:
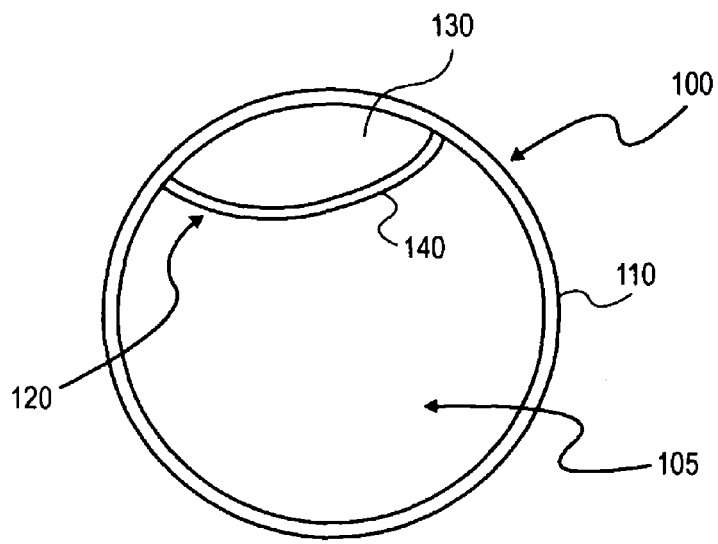
FIG. 1 shows a cross-sectional schematic front view of a blood vessel including a vulnerable plaque.

FIG. 1 shows a cross-sectional view of a blood vessel, such as a coronary artery. Blood vessel 100 includes vessel wall 110 defining lumen 105 therethrough. Formed within lumen 105 of blood vessel 100 is vulnerable plaque 120. Vulnerable plaque 120 includes core 130 surrounded by fibrous cap 140. Core 130, in an unmodified state, includes lipids, cholesterol crystals, cholesterol esters, macrophages, and other cells. Core material 130 in an untreated state is highly thrombogenic and only fibrous cap 140 prevents release of the thrombogenic materials.

Figure 2:
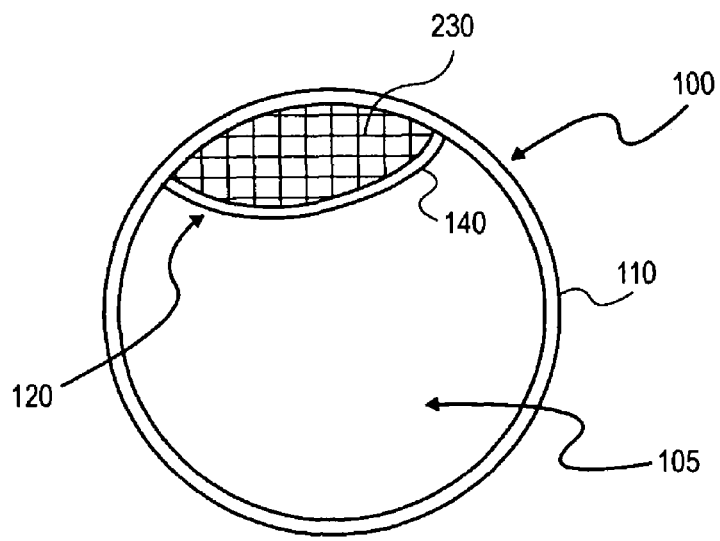
FIG. 2 shows a cross-sectional schematic front view of a vulnerable plaque where a core of the vulnerable plaque has been modified by a treatment agent.

FIG. 2 shows blood vessel 100 following the modification of the core material of vulnerable plaque 120. In one embodiment, a composition is introduced into vulnerable plaque 120 to immobilize the core material. Representatively, the core material may be immobilized by the introduction into vulnerable plaque 120 of a cross-linking agent. Cross-linking agents, in one sense, are agents that link two or more molecules or cells. In one embodiment, the cross-linking agents described herein are introduced in a form such that they cross-link core material of a vulnerable plaque. In one sense, the cross-linking agents may form a network of linked lipid cells within vulnerable plaque 120. In this manner, the core material of vulnerable plaque 120 may be rendered substantially, predominantly, or totally immobile and thus less thrombogenic. FIG. 2 shows vulnerable plaque 120 having modified (immobilized) core material 230.

In one embodiment, a suitable agent for cross-linking the core material of a vulnerable plaque is a glutaraldehyde. Another suitable compound is a polyepoxy. An example of a suitable polyepoxy is ethylene glycol diglycidyl ether. Ethylene glycol diglycidyl either is commercially available as DENACAL EX-810™ for Nagase Chemtex Corporation of Tatsuno City Hyogo Japan. In another embodiment, a suitable cross-linking agent is a natural compound, genipin. In another embodiment, the cross-linking agent is CNBr-activated sepharose. Each of the noted agents or compounds may be used alone or in combination.

In one embodiment, the cross-linking agents are introduced into a blood vessel in liquid form and given the opportunity or caused to diffuse or migrate into a vulnerable plaque. In this manner, the fibrous cap of the vulnerable plaque is not disturbed. Thus, in one embodiment, the cross-linking agent(s) are of a molecular size such that the cross-linking agent(s) is/are capable of diffusing or migrating through a fibrous cap of a vulnerable plaque.

Figure 3:
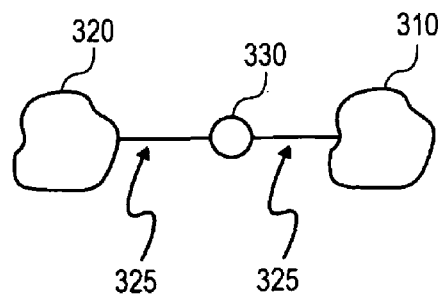
FIG. 3 shows a representative molecular level cross-linking of lipids of a vulnerable plaque core.

FIG. 3 shows a representation of a cross-linking event. FIG. 3 shows lipid cell 310 and lipid cell 320 that might be present in core material of a vulnerable plaque. In this embodiment, lipid cell 310 and lipid cell 320 are connected, such as by a covalent bond connection to cross-linker 330. Cross-linker 330, in one embodiment, is selected from a glutaraldehyde, a polyepoxy, genipin and CNBr-activated sepharose. While not wishing to be bound by theory, it is believed lipid cells of the core material have surface amine groups available for chemical bonding. Thus, one of the noted cross-linking agents may cross-link to lipid cells through covalent bonds 325 formed between the amine groups on different lipid cells. Since the cross-linking event occurs within a vulnerable plaque, the lumen of the blood vessel including the vulnerable plaque is not occluded by the cross-linking event.

Each of the above-referenced cross-linking agents is capable of achieving or inducing a cross-linking event. Each of the treatment agents may be delivered without a cross-linkable monomer or polymer and thus all or a substantial amount of the cross-linking agent is available to cross-link a material of the core of a vulnerable plaque.

To increase the immobilization or fixation time of a core material of a vulnerable plaque, an accelerator may be introduced. An example of a suitable accelerator is salicylic acid. Salicylic acid can increase the reaction time of the noted cross-linking agents (e.g., the time to immobilize the vulnerable plaque tissue), particularly when administered in an alkaline pH. A preferable pH range is on the order of 10 to 12. A representative amount of salicylic acid as an accelerator is on the order of 0.1 percent to one percent accelerator to fixation agent.

The accelerator may be separately introduced into the vulnerable plaque, such as before or after the introduction of a cross-linking agent or simultaneously with the cross-linking agent (such as in a mixture). In one embodiment, a mixture of a cross-linking agent and an accelerator is prepared on site moments before introduction into a blood vessel to minimize the possible cross-linking of the mixture prior to introduction.

In addition to an accelerator, additional therapeutic compounds may alternatively or additionally be introduced into a vulnerable plaque. Representative therapeutic compounds include those that inhibit a vulnerable plaque from growing. Example include enzyme inhibitors and cytotoxic agents.

In one embodiment, the combination of a treatment agent, an accelerator, and any other therapeutic compound for introduction into a vulnerable plaque may be provided as a kit. Representatively, a kit may include separate amounts of each of a treatment agent (a cross-linking agent), an accelerator, and any other optional therapeutic agents. The agent(s) and accelerator may be in a form and dosage suitable for direct infusion into a blood vessel. Instructions may also be provided on infusion of treatment agent(s) or combining treatment agents and/or accelerators. In another embodiment, a kit may include a catheter assembly for delivering the treatment agent to a blood vessel.

Figure 4:
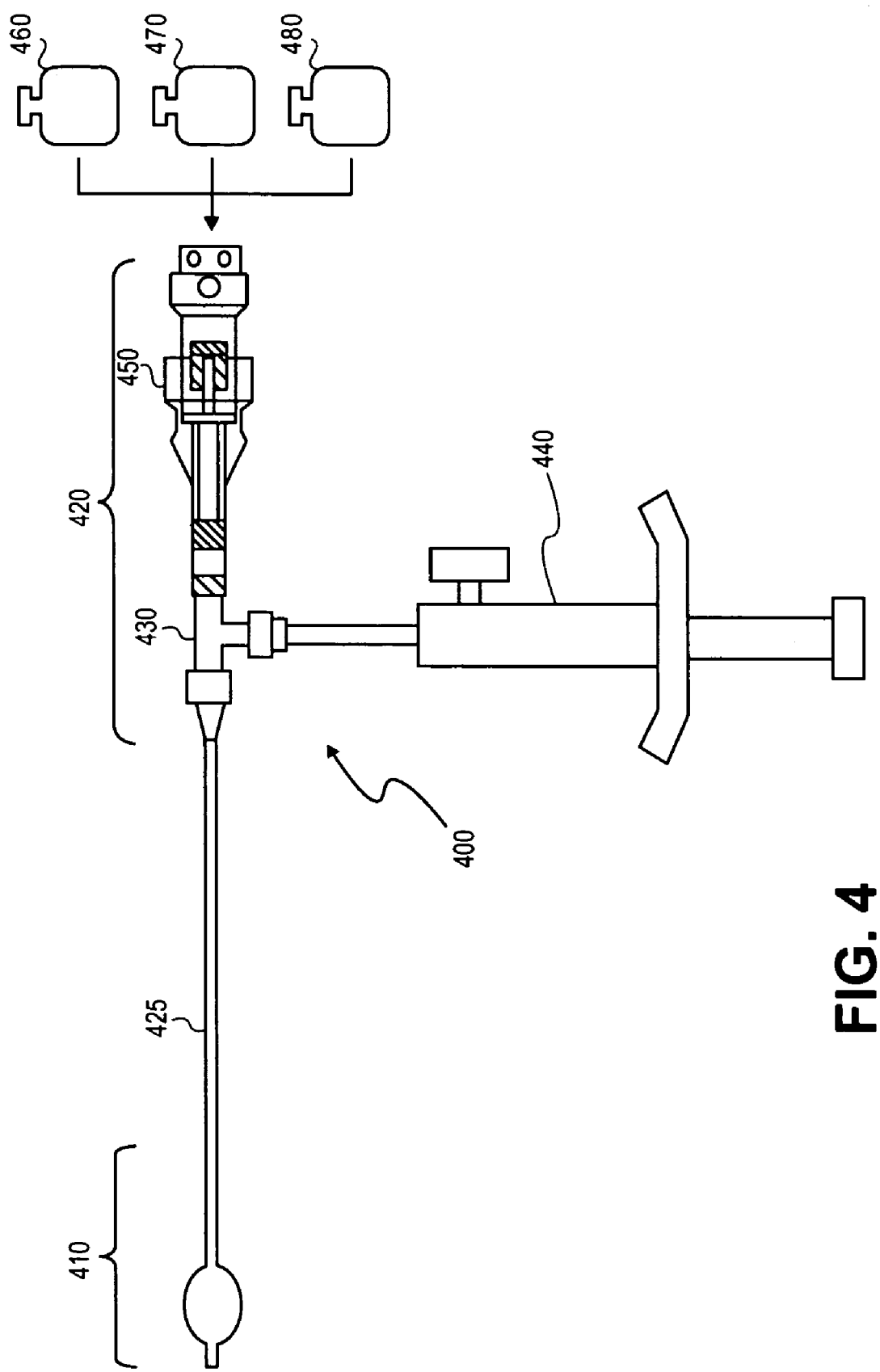
FIG. 4 shows a schematic side view of a tri-lumen shaft catheter assembly.

FIG. 4 shows a side view of an embodiment of a catheter assembly suitable for introducing a treatment agent into a blood vessel. In this embodiment, catheter assembly 400 includes distal portion 410 for insertion into a body lumen, such as a blood vessel, and portion 420 intended to remain external to a patient when catheter assembly 400 is in use. Catheter assembly 400 includes primary cannula or tubular member 425 extending from proximal portion 420 through distal portion 410. In one embodiment, primary cannula 425 has a length such that catheter assembly 400 may be percutaneously inserted into either a femoral artery or a radial artery and advanced to a coronary artery (e.g., left coronary artery, left anterior descending artery, right coronary artery, etc.).

In one embodiment, catheter assembly 400 accommodates three cannulas (a three-lumen shaft). FIG. 5 illustrates a magnified view of distal portion 410 of catheter assembly 400. FIG. 6 shows a cross-section of catheter assembly, through line A-A' of FIG. 5. Referring to FIG. 5 and FIG. 6, three cannulas or tubular members are shown within a lumen of primary cannula 425. The cannulas include guidewire cannula 530, inflation cannula 540, and infusion cannula 550. Each cannula has a lumen therethrough.

FIG. 5 also shows balloon 520 connected to primary cannula 425. Balloon 520 is illustrated in an inflated state. Balloon 520 may be inflated through inflation cannula 540. Inflation cannula 540 extends through primary cannula 425 from proximal portion 420 and distally terminates within balloon 520. In one embodiment, balloon 520 is selectively inflatable through inflation cannula 540 to dilate from a collapsed configuration to a desired and controlled expanded configuration. Balloon 520 can be selectively inflated by supplying a fluid (e.g., liquid) into a lumen of inflation cannula 540 at a predetermined rate of pressure. Likewise, balloon 520 is selectively deflatable to return to a collapsed configuration or a deflated profile.

Balloon 520 can be made from various materials, including, but not limited to, polymers and copolymers of polyolefins, polyamides, polyester and the like. The specific material employed should be compatible with the inflation or expansion fluid and must be able to tolerate the pressures that are developed within balloons 520. One suitable material is an elastomeric nylon, such as PEBAX 63D™, a condensation polymerized polyether block polyamide.

A wall of balloon 520 can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and re-cross a desired region of interest and low susceptibility to defects caused by handling. By way of example, not limitation, a suitable thickness of a balloon wall can be in the range of 0.0005 inches to 0.002 inches, the specific specifications depending on, among other considerations, the anatomy and size of the target lumen in which balloon 520 is to be inserted.

As noted above, catheter assembly 400 also includes guidewire cannula 530 disposed through at least a portion of primary cannula 425. Guidewire cannula 530 allows catheter assembly 400 to be fed and maneuvered over a guidewire (not shown). In one embodiment, guidewire cannula 530 extends the length of primary cannula 425 from proximal portion 420 of catheter assembly 400 to distal portion 410. Representatively, in a typical procedure, the guidewire may be initially placed through a region of interest in a physiological lumen (e.g., a blood vessel) and catheter assembly 400 is advanced, possibly through a guide catheter, on/over the guidewire to or through a region of interest in an over the wire (OTW) fashion. In another embodiment, catheter assembly 400 is a rapid exchange (RX) type catheter assembly and only a portion of catheter assembly 400 (a distal portion) is advanced over the guidewire. In rapid exchange catheters, typically the guidewire cannula/lumen extends from the distal end of the catheter to a proximal guidewire port spaced distally from the proximal end of the catheter. The proximal guidewire port is typically spaced a substantial distance from the proximal end of the catheter.

As also mentioned above, primary cannula 425 includes infusion cannula 550. Infusion cannula 550 extends from proximal portion 420 through distal portion 410 of catheter assembly 400. In this embodiment, infusion cannula 550 extends beyond a distal portion of balloon 520, defining an infusion or dispensing port.

Infusion port 555 has a position distal to balloon 520. In the illustrated embodiment, infusion port 555 is in the distal-most end of the catheter. In other embodiments (not shown), infusion port 555 could be one or more lateral ports in the sidewall of the catheter shaft. In this manner, balloon 520 is placed in a blood vessel longitudinally adjacent and either downstream or upstream to the vulnerable plaque to occlude blood flow along the vulnerable plaque. Balloon 520 may be used to occlude the blood vessel and minimize blood flow during a procedure to treat (e.g., modify, immobilize, etc.) the vulnerable plaque. In the embodiment shown in FIGS. 4-6, balloon 520 could be placed upstream of a vulnerable plaque to occlude flow along the vulnerable plaque. A treatment agent could then introduced into the blood vessel through infusion port 555.

In the embodiment shown in FIGS. 4-6, each of guidewire cannula 530 and inflation cannula 540 extend beyond balloon 520. It is appreciated that a guidewire may or may not be in place during infusion of a treatment agent through a lumen of inflation cannula 540. In another embodiment, rather than having a separate infusion cannula, a guidewire cannula may be used for a guidewire and providing a lumen for a treatment agent. Representatively, in the assembly shown in FIGS. 4-6, catheter assembly 400 would be placed at a region of interest using a guidewire. After placement, the guidewire would be removed and a treatment agent source (reservoir) connected to a proximal end of guidewire cannula 530 to deliver the treatment agent through a lumen of guidewire cannula 530.

Referring again to the embodiment shown in FIG. 4, proximal portion 420 of catheter assembly 400 includes indeflator 440 for introducing a liquid into inflation cannula 540. In one embodiment, indeflator 440 introduces an inflation fluid into a lumen of cannula 540 to inflate balloon 520 at a predetermined rate of pressure. FIG. 4 also shows indeflator 450 capable of introducing a treatment agent into a lumen of infusion cannula 550. In one embodiment, indeflator 450 is a controlled volume indeflator such that a predetermined volume of the treatment agent may be introduced into a lumen of infusion cannula 550 and therefore at a treatment site. FIG. 4 illustrates several reservoirs that may be connected to indeflator 450. Reservoir 460 contains, for example, a treatment agent such as a glutaraldelhyde, a polyepoxy, a natural compound such as genipin, or an activated sepharose. Optional reservoir 470 contains an accelerator such as salicylic acid. Optional reservoir 480 contains a therapeutic agent other than a cross-linking agent. In one embodiment, where multiple agents are to be delivered from multiple reservoirs, the reservoirs may be sequentially connected to indeflator 450.

In the embodiment shown in FIG. 4, indeflator 440 is shown in an offset or lateral position relative to primary cannula 425. In another embodiment, indeflator 440 and a proximal portion of inflation cannula 540 may be arranged coaxially with primary cannula 425 similar to infusion cannula 550 and indeflator 450.

In the embodiment described with reference to FIG. 4, FIG. 5 and FIG. 6, catheter assembly 400 includes a balloon having as at least one purpose to occlude a blood vessel at a position proximal to a treatment site (e.g., a position proximal to a vulnerable plaque). In this manner, infusion cannula 550 and port 555 is extended distally beyond a distal end of the balloon. In another embodiment, it may be desirable to place an occluding feature, such as an occluding balloon at (e.g., radially adjacent) a treatment site (e.g., at a vulnerable plaque). In this embodiment, the treatment agent would be introduced through the occluding feature.

FIG. 7 and FIG. 8 show an alternative embodiment of distal portion 410 of catheter assembly 400, including a balloon having a porous portion and an infusion port within the balloon. FIG. 7 shows balloon 720 connected to primary cannula 425. Guidewire cannula 730 extends beyond a distal end of balloon 720. Infusion cannula 750 terminates within balloon 720 at infusion port 755. In this embodiment, treatment agent will be introduced at a proximal end of infusion cannula 750, through a lumen of infusion cannula 750 to inflate balloon as well as to migrate to a vulnerable plaque through a porous portion of balloon 720. Since a treatment agent will be used to inflate balloon 720, a separate inflation cannula/lumen is not necessary. In alternate embodiment, catheter assembly may include an infusion cannula and an inflation cannula.

In one embodiment, balloon 720 includes porous portion 725. In this embodiment, balloon 720 also includes proximal skirt 770 connected to primary cannula 425, medial working length 775, and distal skirt 780 connected to distally extending guidewire cannula 730. In one embodiment, porous portion 725 may make up a portion of less than the entire inflatable portion of balloon 720. Porous portion 725 in one embodiment, for example, extends only partially around the circumference of balloon 720. FIG. 8 shows a cross-section through line A-A' of FIG. 7 and illustrates porous portion 725 extending partially around the circumference of balloon 720. In one embodiment, porous portion 725 extends a working length of balloon 720 (e.g., the length of medial working length 775), ranging in length from eight millimeters (mm) to 28 mm depending on the length of a vulnerable plaque. In another embodiment, porous portion 725 extends only partially around the circumference of balloon 720 and extends a length less than the length of medial working length 775 of balloon 720.

A porous balloon or a balloon having a porous portion may be made from expanded polytetrafluoroethylene (ePTFE). A balloon having a porous portion of ePTFE may be made with pore sizes on the order of five microns (μm) to 40 μm. One way to form a partial porosity ePTFE balloon is by masking a desired porous portion with a pressure sensitive tape such as Scotch tape and impregnating the remaining portion of balloon with a solution of an elastomeric polymer such as styrene-butadiene-styrene elastomer, silicone-polyurethane copolymer, or polyurethane, etc. Another way to form a non-ePTFE balloon that has a porous portion is to create multiple holes range from 25 to 250 micrometers on a balloon surface via mechanical or chemical means.

In the above described embodiment, infusion cannula 750 delivers treatment agent to an interior of balloon 720 to inflate balloon 720. The treatment agent migrates from balloon 720 through pores in porous portion 725 of balloon 720. It is appreciated that other configurations are also possible. For example, a catheter assembly may include a separate inflation cannula and an infusion cannula, with the inflation cannula extending into a first balloon and the infusion cannula extending into a second balloon disposed on/over the first balloon. In this manner, the first balloon may be used to occlude at least a portion of a vessel and the second balloon may serve to partially occlude the vessel and to deliver the treatment agent. In another embodiment, two balloons may be used and fed by a single infusion cannula. An infusion cannula may extend into a first balloon that is porous (e.g., contains micropores) and allows a treatment agent to migrate from an interior of the first balloon into an interior of the second balloon on/over the first balloon. The second balloon has a portion that is also porous allowing the treatment agent to migrate from the interior of the second balloon. One advantage of this configuration is that the second balloon provides a protective effect to a vessel from possible pressurized streams of treatment agent that may come from the first inner balloon.

Figure 9:
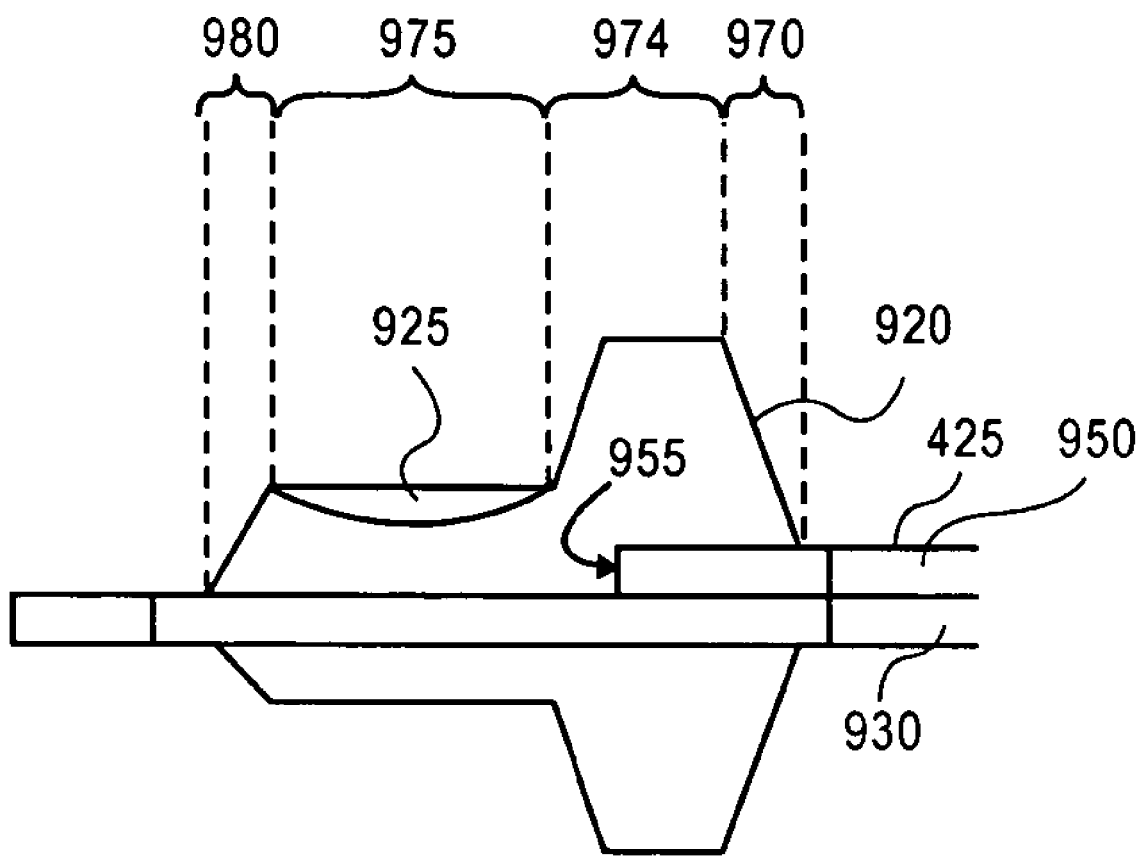
FIG. 9 shows a cross-sectional schematic side view of another embodiment of a distal portion of the catheter assembly of FIG. 4.

In the embodiment described with reference to FIG. 7 and FIG. 8, a balloon is placed so that a portion of its working length is at or along a fibrous cap of a vulnerable plaque. Care may be necessary to not contact the fibrous cap or minimize the force of contact on the fibrous cap when the balloon is inflated. FIG. 9 shows an alternative embodiment of distal portion 410 of catheter assembly 400, including a balloon having a porous portion and an infusion port within the balloon. FIG. 9 shows balloon 920 connected to primary cannula 425. Guidewire cannula 930 extends beyond a distal end of balloon 920. A distal end of infusion cannula 950 terminates within balloon 920 at infusion port 955. Treatment agent may be introduced at a proximal end of infusion cannula 950 through infusion cannula 950, and through infusion port 955 to inflate balloon 920.

In the embodiment illustrated in FIG. 9, balloon 920 includes proximal skirt 970 connected to primary cannula 425 and distal skirt 980 connected to guidewire cannula 930. Balloon 920 also includes first medial working length portion 974 and second medial working length portion 975 connected to proximal skirt 970 and distal skirt 980, respectively. In an inflated state, first medial working length portion 974 has a greater diameter than second medial working length portion 975 and is generally more elastic than second medial working length portion 975. One way to form first medial working length portion 974 having a greater elasticity than second medial working length portion 975 to form a generally inelastic medial working length of balloon 920 having a length including both first medial working length portion 974 and second medial working length portion 975 and then impregnate an elastomer into first medial working length portion 974.

In one embodiment, first medial working length portion 974 is capable of being inflated to a diameter of a target blood vessel while second medial working length portion 975 may be inflated to a diameter less than a diameter of a target blood vessel and preferably less than a diameter of a blood vessel including a vulnerable plaque. In one embodiment, catheter assembly 400 is placed so that first medial working length portion 974 of balloon 920 is upstream of a vulnerable plaque and can be inflated to occlude a target blood vessel without contacting a vulnerable plaque.

First medial working length portion 974 has a length dimension suitable to provide the structural integrity to occlude blood flow. Representatively, a length on the order of a few millimeters is sufficient.

Second medial working length portion 975 of balloon 920 has a length, in one embodiment, approximately equivalent to a length of a vulnerable plaque. A representative length for second medial working length portion 975 is on the order of 8 mm to 28 mm. Second medial working length portion 975 includes porous portion 925 that may be similar to porous portion 725 of balloon 720 as described above with reference to FIG. 7 and FIG. 8 and the accompanying text. Porous portion 925 may extend only partially around the circumference of balloon 920 and may extend the entire length of second medial working length portion 975. A treatment agent delivered through infusion cannula 950 at infusion port 955 may migrate through porous portion 925 of second medial working length portion 975 and be delivered to a vulnerable plaque.

To locate a vulnerable plaque within a blood vessel, various imaging techniques may be used. Such imaging techniques include intraluminal techniques such as OCT and IVUS. Once a treatment site including a vulnerable plaque has been identified, a catheter assembly, such as the catheter assembly described with reference to FIG. 4, FIG. 5 and FIG. 6 or FIG. 4, FIG. 7 and FIG. 8 or FIG. 4 and FIG. 9 may be introduced into the blood vessel.

Figure 10:
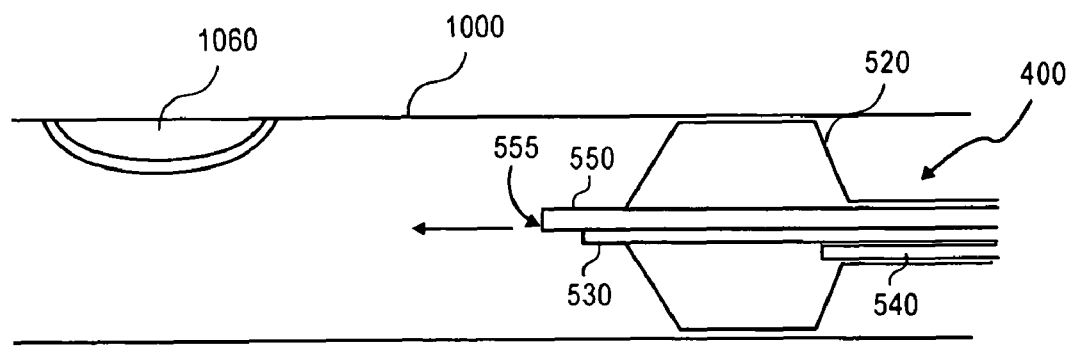
FIG. 10 shows a cross-sectional schematic side view of a blood vessel having an embodiment of a catheter assembly described with reference to FIGS. 4-6 disposed therein and dispensing a treatment agent at a point proximal to a vulnerable plaque.

FIG. 10 shows a cross-sectional side view of a blood vessel having a vulnerable plaque therein and a treatment device within the blood vessel. Representatively, treatment device 400, as described above with reference to FIG. 4, FIG. 5 and FIG. 6, includes balloon 520 that occludes blood vessel 1000 at a point proximal to the treatment site, or proximal to vulnerable plaque 1060. A treatment agent is then infused into blood vessel 1000 through dispensing port 555 at a point distal to balloon 520. The treatment agent migrates or diffuses through the thin fibrous cap of vulnerable plaque 1060 to modify the core.

Figure 11:
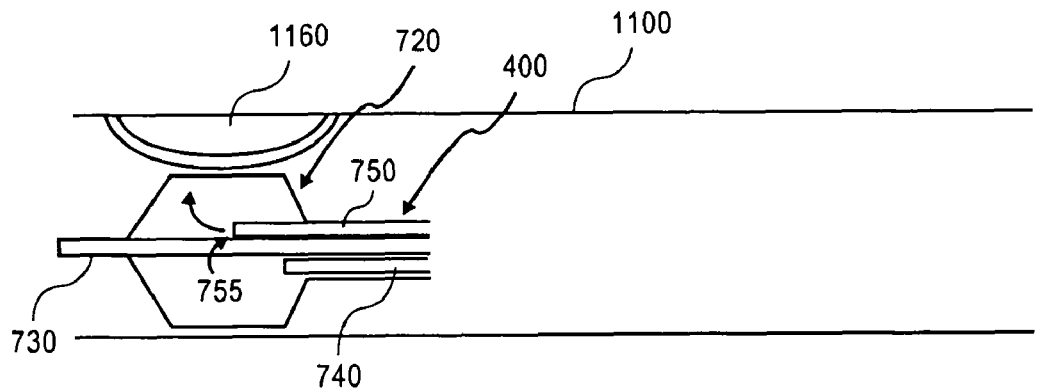
FIG. 11 shows a cross-sectional schematic side view of a blood vessel having an embodiment of a catheter assembly described with reference to FIG. 4 and FIGS. 7-8 disposed therein and dispensing a treatment agent with an occlusion feature at the vulnerable plaque.

FIG. 11 shows a cross-sectional side view of a blood vessel having a vulnerable plaque therein and another embodiment of a treatment device disposed in the blood vessel. In this embodiment, treatment device 400 is, for example, a catheter assembly similar to the assembly described above with reference to FIG. 4, FIG. 7 and FIG. 8 and the accompanying text. Treatment device 410 includes balloon 720. Balloon 720 is shown in an inflated state within blood vessel 1100. Balloon 720 is positioned, in this embodiment, with a working length, at a treatment site including vulnerable plaque 1160. In one embodiment, balloon 720 is inflated at a low pressure (such as below four atmospheres or even below one atmosphere) and a controlled rate. In one embodiment, balloon 720 is inflated to a diameter that is less than an interior diameter of vulnerable plaque 1160 and preferably does not contact vulnerable plaque 1160.

In this embodiment, balloon 720 includes porous portion 725 along the working length of balloon 720. Infusion port 755 of, for example, an infusion cannula 755 is located within balloon 720. A treatment agent is introduced through infusion port 755. The treatment agent will migrate through the porous portion of balloon 720 and may migrate or diffuse into vulnerable plaque 1060.

Where porous portion 725 of balloon 720 extends around less than the entire circumference and/or extends less than the working length of balloon 720, it may be desirable to align (position) the porous portion at vulnerable plaque 1160. One technique for such aligning or positioning includes placement of an imaging device, such as an OCT device through a guidewire cannula of catheter assembly 400. Vulnerable plaque 1160 may be identified with the imaging device and balloon 720 rotated or positioned proximally or distally so that porous portion 725 of balloon 720 aligns with (is positioned on or at) vulnerable plaque 1160.

Figure 12:
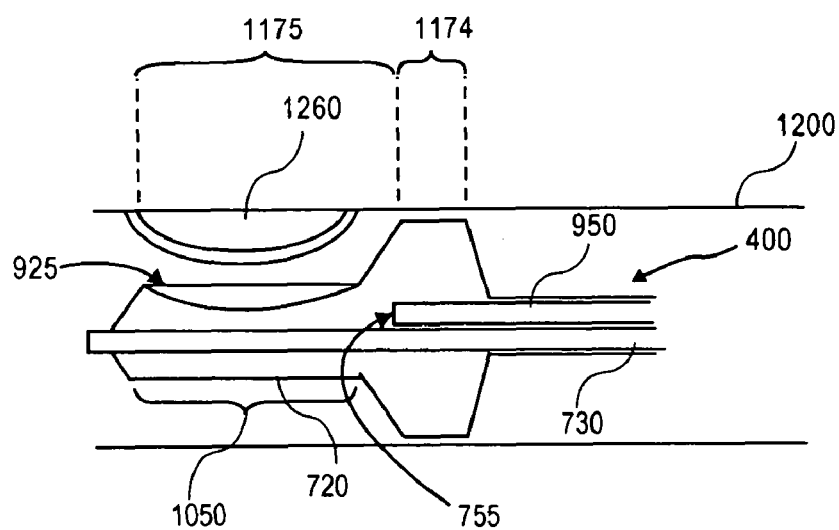
FIG. 12 shows a cross-sectional schematic side view of a blood vessel having an embodiment of a catheter assembly described with reference to FIG. 4 and FIG. 9 disposed therein and dispensing a treatment agent with an occlusion feature at the vulnerable plaque.

FIG. 12 shows a cross-sectional side view of a blood vessel having a vulnerable plaque therein and a treatment device within the blood vessel. Representatively, treatment device 400, as described above with reference to FIG. 4 and FIG. 9, includes balloon 920 including first medial working length portion 974 and second medial working length portion 975. Second medial working length portion 975 is placed along a vulnerable plaque and first medial working length portion is located proximally adjacent vulnerable plaque 1260. Balloon 920 is inflated with a treatment agent delivered through infusion port 955 of infusion cannula 950. First medial working length elastic portion 974 inflates to contact an inner wall of blood vessel 1200 or to block blood flow, while second medial working length portion 975 of balloon 920 will not significantly inflate at least not significantly enough to come in contact with or damage vulnerable plaque 1260. A treatment agent introduced through infusion port 955 will migrate through porous portion 925 of balloon 920 and may migrate or diffuse into vulnerable plaque 1260.

In another embodiment, the migration or diffusion of a treatment agent into a vulnerable plaque, for example, according to the embodiments described in FIG. 11 and FIG. 12 may be assisted. Representative assist techniques include, but are not limited to, electrotransport techniques. For example, a piezoelectric microchip under/on balloon 720, with a selected frequency, amplitude, duty cycle, and waveform will emit ultrasonic frequency around the detected of vulnerable plaque surface of an arterial wall to facilitate the diffusion of treatment agent into a vulnerable plaque. Another way to facilitate the diffusion of treatment agent into a vulnerable plaque is through iontophoresis, such as by employing a silver/silver chloride electrode under a porous balloon. An electrical potential may be created within the balloon to drive treatment agent out of the balloon and into the vulnerable plaque.

In the above embodiments, devices and techniques for externally introducing a treatment agent into a vulnerable plaque are described. It is appreciated that the treatment agents may be introduced in various other means. Representatively, a treatment agent may be injected into the vulnerable plaque using, for example, a needle catheter. Concern in this case may be with rupturing the vulnerable plaque with the injection. Possible techniques for minimizing such rupture include supporting the vulnerable plaque with a balloon or stent during injection.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
   introducing a treatment device via a transluminal route within a blood vessel to a treatment site comprising a vulnerable plaque having a fibrous cap; and
   while introducing, dispensing a liquid treatment agent comprising a compound through the treatment device; such that diffusing the treatment agent through the fibrous cap and into a core of the vulnerable plaque, the compound having a property that tends to modify a mobility of a core material of the vulnerable plaque from highly thrombogenic to generally non-thrombogenic, wherein the compound comprises a polyepoxy.

2. The method of claim 1, wherein the compound comprises a property capable of cross-linking at least two components of the core material of the vulnerable plaque to immobilize lipids of the core material.

3. The method of claim 1, wherein the liquid treatment agent further comprises a glutaraldehyde.

4. The method of claim 1, wherein the polyepoxy comprises ethylene glycol diglycidyl ether.

5. The method of claim 1, wherein the liquid treatment agent further comprises genipin.

6. The method of claim 1, wherein the liquid treatment agent further comprises CNBr-activated sepharose.

7. The method of claim 1, wherein the treatment agent comprises a first treatment agent, the method further comprising dispensing a different second treatment agent.

8. The method of claim 1, further comprising, prior to dispensing:
   occluding the blood vessel at a site proximal to the treatment site.

9. The method of claim 1, further comprising, prior to dispensing:
   occluding the blood vessel at a portion of the treatment site.

10. The method of claim 9, wherein occluding the blood vessel comprises inflating a balloon a portion of which has a property that is porous to the treatment agent.

11. The method of claim 10, wherein the portion of the balloon that is porous is less than the entire portion of the balloon, the method further comprising:
    aligning that portion of the balloon that is porous with a portion of the blood vessel comprising the vulnerable plaque; and
    dispensing the treatment agent through the balloon.

12. A method comprising:
    introducing a treatment device via a transluminal route within a blood vessel to a treatment site comprising a vulnerable plaque; and
    while introducing, dispensing a first treatment agent and a second treatment agent through the treatment device and into a core of the vulnerable plaque, wherein the first treatment agent comprises a polyepoxy and the second treatment agent has a property that accelerates the cross-linking of components of the core material of the vulnerable plaque.

13. A kit comprising:
a first liquid treatment agent capable of diffusing or migrating into a core of a vulnerable plaque and comprising a property capable of modifying a mobility of an existing core material of the vulnerable plaque from highly thrombogenic to generally non-thrombogenic, wherein the first liquid treatment agent comprises a polyepoxy; and
a different second liquid treatment agent that has a property that accelerates the cross-linking of components of an existing core material of a vulnerable plaque.

14. The kit of claim 13, wherein the first treatment agent further comprises a glutaraldehyde.

15. The kit of claim 13, wherein the polyepoxy comprises ethylene glycol diglycidyl ether.

16. The kit of claim 13, wherein the first treatment agent further comprises genipin.

17. The kit of claim 13, wherein the first treatment agent further comprises CNBr-activated sepharose.

18. The kit of claim 13, further comprising:
a catheter suitable for traversing a blood vessel and having a length dimension suitable for placement at a treatment site within the blood vessel from an externally accessible point on a patient.

19. The kit of claim 18, wherein the catheter comprises a dispensing port and a feature capable of occluding a portion of a blood vessel at a point proximal to the dispensing port.

20. The kit of claim 18, wherein the catheter comprises a feature capable of occluding a portion of the blood vessel at a treatment site and a dispensing port at the feature.

21. The kit of claim 20, wherein the feature comprises a balloon comprising a portion having a property that is porous to the treatment agent.

22. The kit of claim 21, wherein the portion of the balloon having a property that is porous to the treatment agent is less than the entire portion.

23. A liquid composition in a form and concentration suitable for dispensing through a catheter into a blood vessel, the composition comprising a first treatment agent comprising a polyepoxy that, once delivered into a blood vessel, includes a compound comprising a property capable of modifying the mobility of a content of a vulnerable plaque from highly thrombogenic to generally non-thrombogenic, and a second treatment agent that has a property that accelerates a cross-linking of components of a content of a vulnerable plaque.

24. The composition of claim 23, wherein the compound has a property capable of cross-linking components of the content of the vulnerable plaque to immobilize lipids of the content.

25. The composition of claim 23, wherein the first treatment agent further comprises a glutaraldehyde.

26. The composition of claim 23, wherein the polyepoxy comprises ethylene glycol diglycidyl ether.

27. The composition of claim 23, wherein the first treatment agent further comprises genipin.

28. The composition of claim 23, wherein the first treatment agent further comprises CNBr-activated sepharose.

29. A system comprising:
a first reservoir containing a first flowable substance comprising a liquid cross-linking agent having a property capable of modifying a content of a core of a vulnerable plaque from highly thrombogenic to generally non-thrombogenic, wherein the substance comprises a polyepoxy;
second reservoir containing an accelerating agent that has a property to accelerate a cross-linking of components of a content of a core of a vulnerable plaque; and
a cannula comprising a lumen in fluid communication with either the first flowable substance in the first reservoir or the accelerating agent in the second reservoir and a distal end portion defining an opening allowing passage out of the distal end portion of the cannula.

30. The system of claim 29, wherein the cannula has a dimension suitable for traversing a blood vessel and having a length dimension suitable for placement at a treatment site within the blood vessel from an externally accessible point on a patient.

31. The system of claim 29, wherein the property of the content of the vulnerable plaque comprises mobility.

32. The system of claim 31, further comprising a third reservoir comprising a glutaraldehyde.

33. The system of claim 31, wherein the polyepoxy comprises ethylene glycol diglycidyl ether.

34. The system of claim 31, further comprising a third reservoir comprising genipin.

35. The system of claim 31, further comprising a third reservoir comprising CNBr-activated sepharose.

36. The system of claim 29, further comprising a feature capable of occluding a portion of a blood vessel coupled to the cannula at a point proximal to opening defined in the distal end portion.

37. The system of claim 29, further comprising a feature capable of occluding a portion of a blood vessel at a treatment site and coupled to the cannula at a point such that the feature and the opening defined in the distal end portion are coextensive.

38. The system of claim 37, wherein the feature comprises a balloon comprising a portion having a property that is porous to the treatment agent.

39. The system of claim 38, wherein the portion of the balloon having a property that is porous to the treatment agent comprises a portion of a working length of the balloon.

40. The system of claim 29, wherein opening is defined at an end of the distal end portion.

41. A method comprising:
introducing a treatment device via a transluminal route within a blood vessel to a treatment site comprising a vulnerable plaque having a fibrous cap; and
while introducing, modifying a mobility of an existing core material of the vulnerable plaque from highly thrombogenic to generally non-thrombogenic with a liquid treatment agent comprising a polyepoxy dispensed from the treatment device; the liquid treatment agent diffusing through the fibrous cap of the vulnerable plaque.

42. The method of claim 41, wherein the compound comprises a property capable of cross-linking at least two components of the core material of the vulnerable plaque to immobilize lipids of the core material.

43. The method of claim 41, wherein the liquid treatment agent further comprises a glutaraldehyde.

44. The method of claim 41, wherein the polyepoxy comprises ethylene glycol diglycidyl ether.

45. The method of claim 41, wherein the liquid treatment agent further comprises genipin.

46. The method of claim 41, wherein the liquid treatment agent further comprises CNBr-activated sepharose.

47. The method of claim 41, wherein the treatment agent comprises a first treatment agent, the method further comprising dispensing a different second treatment agent.

48. The method of claim 41, further comprising, prior to dispensing:

occluding the blood vessel at a site proximal to the treatment site.

49. The method of claim 41, further comprising, prior to dispensing:

occluding the blood vessel at a portion of the treatment site.

50. The method of claim 49, wherein occluding the blood vessel comprises inflating a balloon a portion of which has a property that is porous to the treatment agent.

51. The method of claim 50, wherein the portion of the balloon that is porous is less than the entire portion of the balloon, the method further comprising:

aligning that portion of the balloon that is porous with a portion of the blood vessel comprising the vulnerable plaque; and dispensing the treatment agent through the balloon.

52. A method comprising:

introducing a treatment device via a transluminal route within a blood vessel to a treatment site comprising a vulnerable plaque; and modifying a mobility of an existing core material of the vulnerable plaque from highly thrombogenic to generally non-thrombogenic with a first liquid treatment agent comprising a polyepoxy and a second treatment agent dispensed from the treatment device, wherein the second treatment agent has a property that accelerates a cross-linking of components of a core material of a vulnerable plaque.

* * * * *